United States Patent
Fang et al.

(10) Patent No.: US 10,793,896 B2
(45) Date of Patent: Oct. 6, 2020

(54) METHODS FOR RT-PCR COMPRISING AN ANIONIC POLYMER

(71) Applicant: Qiagen GmbH, Hilden (DE)

(72) Inventors: Nan Fang, Hilden (DE); Andreas Missel, Hilden (DE)

(73) Assignee: QIAGEN GmbH, Hilden (DE)

( * ) Notice: Subject to any disclaimer, the term of this patent is extended or adjusted under 35 U.S.C. 154(b) by 24 days.

(21) Appl. No.: 15/684,443

(22) Filed: Aug. 23, 2017

(65) Prior Publication Data

US 2017/0356026 A1 Dec. 14, 2017

Related U.S. Application Data

(62) Division of application No. 14/238,801, filed as application No. PCT/EP2012/065793 on Aug. 13, 2012, now Pat. No. 9,758,812.

(30) Foreign Application Priority Data

Aug. 17, 2011 (EP) .................................. 11177730

(51) Int. Cl.
  *C12Q 1/6806* (2018.01)
  *C12Q 1/686* (2018.01)
  *C12N 15/10* (2006.01)
(52) U.S. Cl.
  CPC ....... *C12Q 1/6806* (2013.01); *C12N 15/1096* (2013.01); *C12Q 1/686* (2013.01)
(58) Field of Classification Search
  CPC .............. C12Q 1/686; C12Q 2521/107; C12Q 2527/125; C12Q 1/6806; C12N 15/1096
  See application file for complete search history.

(56) References Cited

U.S. PATENT DOCUMENTS

2004/0219595 A1 11/2004 Lee et al.
2009/0137008 A1 5/2009 Gong et al.

FOREIGN PATENT DOCUMENTS

| EP | 1069190 B1 | 9/2006 |
| EP | 1050587 B1 | 4/2007 |
| WO | 03/064605 A2 | 8/2003 |
| WO | 2010/065924 A1 | 6/2010 |

OTHER PUBLICATIONS

Stratagene Catalog, p. 39 (1988).
Simon, Dawn M. et al. "A Diversity of Uncharacterized Reverse Transcriptases in Bacteria," Nucleic Acids Research, Nov. 12, 2008, pp. 7219-7229, vol. 36 No. 22.
Baba, Masanori et al. "Mechanism of Inhibitory Effect of Dextran Sulfate and Heparin on Replication of Human Immunodeficiency Virus in Vitro," Medical Sciences, Aug. 1988, pp. 6132-6136, vol. 85, Proceedings of the National Academy of Sciences, U.S.A.

*Primary Examiner* — Teresa E Strzelecka
(74) *Attorney, Agent, or Firm* — Rankin, Hill & Clark LLP (57) ABSTRACT

The present invention is directed to methods for the generation of nucleic acids from an RNA template and further nucleic acid replication. Specifically, the invention is directed to the generation and amplification of nucleic acids by reverse transcriptase-polymerase chain reaction (RT-PCR).

5 Claims, 6 Drawing Sheets
Specification includes a Sequence Listing.

Figure 6

METHODS FOR RT-PCR COMPRISING AN ANIONIC POLYMER

CROSS-REFERENCE TO RELATED APPLICATIONS

This application is a division of U.S. application Ser. No. 14/238,801, filed Feb. 13, 2014, now U.S. Pat. No. 9,758,812 B2, which application was a U.S. national stage of PCT/EP2012/065793, filed Aug. 13, 2012, and claims priority to EP 11177730.6, filed Aug. 17, 2011.

FIELD OF THE INVENTION

The present invention is in the fields of molecular biology. The present invention is directed to novel compositions methods and kits useful for the generation of nucleic acids from an RNA template and further nucleic acid replication. Specifically, the invention is directed to the generation and amplification of nucleic acids by reverse transcriptase-polymerase chain reaction (RT-PCR).

BACKGROUND OF THE INVENTION

The detection, analysis, transcription and amplification of nucleic acids are the most important procedures in modern molecular biology. The application of such procedures for RNA analysis is especially important in the investigation of gene expression, diagnosis of infectious agents or genetic diseases, the generation of cDNA and analysis of retroviruses, to name but a few applications. The reverse transcription of RNA, followed by polymerase chain reaction amplification, commonly referred to as RT-PCR, has become widely used for the detection and quantification of RNA.

The RT-PCR procedure involves two separate molecular syntheses: First, the synthesis of cDNA from an RNA template; and second, the replication of the newly synthesized cDNA through PCR amplification. RT-PCR may be performed under three general protocols:
1) Uncoupled RT-PCR, also referred to as two-step RT-PCR.
2) Single enzyme coupled RT-PCR, also referred to as one-step RT-PCR or continuous RT-PCR, in which a single polymerase is used for both the cDNA generation from RNA as well as subsequent DNA amplification.
3) Two (or more) enzyme coupled RT-PCR, in which at least two separate polymerases are used for initial cDNA synthesis and subsequent replication. This is sometimes also referred to as one-step RT-PCR or, alternatively, one-tube RT-PCR.

In uncoupled RT-PCR, reverse transcription is performed as an independent step using buffer and reaction conditions optimal for reverse transcriptase activity. Following cDNA synthesis, an aliquot of the RT reaction product is used as template for PCR amplification with a thermostable DNA polymerase, such as Taq DNA Polymerase, under conditions optimal for PCR amplification.

In coupled RT-PCR, reverse transcription and PCR amplification are combined into a single reaction mixture. Single enzyme RT-PCR utilizes the reverse transcriptase activity of certain DNA polymerases, such as Tth DNA polymerase, whereas two-enzyme RT-PCR typically uses a retroviral or bacterial reverse transcriptase (e.g. AMV-RT, MMLV-RT, HIV-RT, EIAV-RT, RAV2-RT, *Carboxydothermus hydrogenoformans* DNA polymerase or a mutant, variant or derivative thereof), and a thermostable DNA polymerase (e.g. Taq, Tbr, Tih, Tfi, Tfl, Pfu, Pwo, Kod, VENT™, DEEPVENT™, Tma, Tne, Bst, Pho, Sac, Sso, ES4 and others or a mutant, variant or derivative thereof).

Coupled RT-PCR provides numerous advantages over uncoupled RT-PCR. Coupled RT-PCR requires less handling of the reaction mixture reagents and nucleic acid products than uncoupled RT-PCR (e.g., opening of the reaction tube for component or enzyme addition in between the two reaction steps), and is therefore less labor-intensive, and time-consuming, and has reduced risk of contamination. Furthermore, coupled RT-PCR also requires less sample, making it especially suitable for applications where the sample amounts are limited (e.g., with FFPE, biopsy, environmental samples).

Although single-enzyme-coupled RT-PCR is easy to perform, this system is expensive to perform, however, due to the amount of DNA polymerase required. In addition, the single enzyme coupled RT-PCR method has been found to be less sensitive than uncoupled RT-PCR, and limited to polymerizing nucleic acids of less than one kilobase pair in length. Coupled RT-PCR systems with two or more enzymes generally show increased sensitivity over the single enzyme system, even when coupled in a single reaction mixture. This effect has been attributed to the higher efficiency of reverse transcriptase in comparison to the reverse transcriptase activity of DNA polymerases (Sellner and Turbett, BioTechniques 25(2):230-234 (1998)).

Although the two-enzyme coupled RT-PCR system is more sensitive than the single-enzyme system, reverse transcriptase has been found to interfere directly with DNA polymerase during the replication of the cDNA, thus reducing the sensitivity and efficiency of this technique (Sellner et al., J. Virol. Methods 40:255-264 (1992)). A variety of solutions to overcome the inhibitory activity of reverse transcriptase on DNA polymerase have been tried, including: increasing the amount of template RNA, increasing the ratio of DNA polymerase to reverse transcriptase, adding modifier reagents that may reduce the inhibitory effect of reverse transcriptase on DNA polymerase (e.g., non homologous tRNA, T4 gene 32 protein, sulphur or acetate-containing molecules), and heat-inactivation of the reverse transcriptase before the addition of DNA polymerase.

Sellner et al. (Nucleic Acids Research 20(7):1487-1490) describe that the detection of viral RNA by polymerase chain reaction requires the prior reverse transcription of the viral RNA. In order to minimize the number of manual manipulations required for processing large numbers of samples, Sellner et al. attempted to design a system whereby all the reagents required for both reverse transcription and amplification can be added to one tube and a single, non-interrupted thermal cycling program can be performed. Whilst attempting to set up such a one-tube system with Taq polymerase and avian myoblastis virus, they noticed a substantial decrease in the sensitivity of detection of viral RNA. They found out a direct interference of reverse transcriptase with Taq polymerase.

All of these modified RT-PCR methods have significant drawbacks, however. Increasing the amount of template RNA is not possible in cases where only limited amounts of sample are available. Individual optimization of the ratio of reverse transcriptase to DNA polymerase is not practicable for ready-to-use reagent kits for one-step RT-PCR. The net effect of currently proposed modifier reagents to relive reverse transcriptase inhibition of DNA polymerization is controversial and in dispute: positive effects due to these reagents are highly dependent on RNA template amounts, RNA composition, or may require specific reverse transcriptase-DNA polymerase combinations (Chandler et al., Appl. and Environm. Microbiol. 64(2):669-677 (1998)). Finally, heat inactivation of the reverse transcriptase before the addition of the DNA polymerase negates the advantages of the coupled RT-PCR and carries all the disadvantages of uncoupled RT-PCR systems discussed earlier. Even if a reverse transcriptase is heat inactivated, it still may confer an inhibitory effect on PCR, likely due to binding of heat-inactivated reverse transcriptase to the cDNA template.

Some improvements to reduce the inhibitory effect of reverse transcriptase on the activity of the polymerase have been made.

In US 2009/0137008 A1, Gong and Wang describe the reduction of the inhibitory effect of reverse transcriptase on DNA polymerase by proteins that bind dsDNA in a non-specific way such as Sso7d, Sac7d, Sac7e or Sso7e and by sulfonic-acid and by sulfonic acid salts.

In EP 1050587 B1, Missel et al. describe the reduction of the inhibitory effect of reverse transcriptase on DNA polymerase by homopolymeric nucleic acids.

Although the methods described by Gong and Wang and Missel et al., respectively, successfully have shown a significant reduction of the inhibitory effect of reverse transcriptase, a further improved specificity and sensitivity of RT-PCR by a more effective reduction of the inhibitory effect of reverse transcriptase is still a need in the art.

Because of the importance of RT-PCR applications, a coupled RT-PCR system, in the form of a generalized ready-to-use composition, which exhibits high specificity and sensitivity, requires a small amount of initial sample, reduces the amount of practitioner manipulation, minimizes the risks of contamination, minimizes the expense of reagents, is not restricted to the use of specific reaction buffers, and maximizes the amount of nucleic acid end product is needed in the art.

SUMMARY OF THE INVENTION

The present invention is directed to novel compositions and methods useful for the generation of nucleic acids from an RNA template and further nucleic acid replication. Specifically, the invention is directed to the generation and amplification of nucleic acids by reverse transcriptase-polymerase chain reaction (RT-PCR), utilizing two or more different polymerases in the presence of an anionic polymer that is not a nucleic acid. The presence of the anionic polymer serves to negate inhibition of the DNA polymerase, which occurs when a composition comprising two or more polymerases, at least one of which having reverse transcriptase activity, is used. The compositions and methods of the present invention are used to generate and replicate DNA molecules complementary to a portion of an RNA template.

The present invention is directed generally to all reaction mixtures that can be used in the generation and replication of a nucleic acid from an RNA template. One embodiment of the present invention is directed to a composition comprising an anionic polymer that is not a nucleic acid and one or more of the following reaction components: a reverse transcriptase, a nucleic acid polymerase, one or more oligonucleotide primers, any one or more nucleotide base, an appropriate buffering agent, a salt solution, or other additives useful in RT-PCR.

The present invention offers several advantages compared to known methods for generating cDNA from an RNA target, including, but not limited to:

permitting coupled RT-PCR, involving one reaction solution and reduced handling of reagents and products;

permitting use of a small initial sample of RNA template;

permitting use of a wide range of different reverse transcriptases;

permitting use of a wide range of different DNA polymerases;

permitting use of a wide range of different reaction mixture buffers and salt solutions, including buffers containing additional specialized reaction additives;

reducing adverse effects on the specificity and product yield, as observed e.g. with tRNA additives;

operating with reagents that are commercially available, easily synthesized, and inexpensive.

The invention thus facilitates the rapid and efficient generation of nucleic acid molecules from a sample containing ribonucleic acids (RNA) as well as the detection and quantitation of RNA molecules. The invention is also useful in the rapid production and amplification of cDNAs that may be used for a variety of industrial, medical and forensic purposes. An anionic polymer according to the present invention is defined as any macromolecule that is not a nucleic acid and that comprises a net charge of at least −1 at the pH used in the enzymatic reactions according to the present invention and an equivalent amount of counter-cations. In one embodiment of the present invention, the net charge of the anionic polymers at the pH used in the enzymatic reaction is in the range from −1 to −10.000, preferable in the range of −5 to −5.000, more preferable in the range of −10 to −1.000 and most preferable in the range of −20 to −200. In all cases, an equivalent amount of counter-ions is present. In one embodiment of the present invention, the anionic polymer is a polysaccharide. In another embodiment of the present invention, the anionic polymer is a polypeptide. In yet another embodiment of the present invention, the anionic polymer is an acid or an anhydride. In a preferred embodiment, the anionic polymer is selected from the group consisting of dextran sulphate, sodium alginate, heparin, carrageen, sodium carboxymethylcellulose, polyphloretin phosphate, poly-L-glutamate, polyacrylic acid, poly(propylacrylic) acid, poly(methyl-vinyl-ether-maleic anhydride, or a mixture of two or more of these anionic polymers. The amount of anionic polymer used for RT-PCR may be greater than 1 µg/ml, preferably between 1 pg/ml to 1 mg/ml, more preferably between 10 pg/ml to 100 µg/ml, most preferably between 1 ng/m to 10 µg/ml. Depending on the anionic polymer used, the concentration of the anionic polymer used for RT-PCR might vary.

The present invention includes compositions containing anionic polymer in higher concentrations as the preferred final concentrations given above, but which are intended to achieve the preferred final concentrations by dilution, e.g. by combination with further components of the reaction mixture.

The reverse transcriptase may be any polymerase that exhibits reverse transcriptase activity. Preferably, the reverse transcriptase is OminiScript™, AMV-RT, MMLV-RT, HIV-RT, EIAV-RT, RAV2-RT, *C. hydrogenoformans* DNA polymerase, SuperScript I™, SuperScript II™ SuperScript III™ or mutants, variants and derivatives thereof having reverse transcriptase activity.

As used herein, mutants, variants and derivatives refer to all permutations of a chemical species, which may exist or be produced, that still retain the definitive chemical activity of that chemical species. Examples include, but are not limited to compounds that may be detectably labelled or otherwise modified, thus altering the compound's chemical or physical characteristics.

In a preferred embodiment, the nucleic acid polymerase may be a DNA polymerase. The DNA polymerase may be any polymerase capable of replicating a DNA molecule. Preferably, the DNA polymerase is a thermostable polymerase useful in PCR. More preferably, the DNA polymerase is Taq, Tbr, Tth, Tih, Tfi, Tfl, Pfu, Pwo, Kod, VENT, DEEPVENT, Tma, Tne, Bst, Pho, Sac, Sso, Poc, Pab, ES4 or mutants, variants and derivatives thereof having DNA polymerase activity.

Oligonucleotide primers may be any oligonucleotide of two or more nucleotides in length. Primers may be random primers, homopolymers, or primers specific to a target RNA template, e.g. a sequence specific primer.

Additional compositional embodiments comprise an anionic polymer and other reaction mixture components such as one or more nucleotides or derivatives thereof. Preferably the nucleotide is a deoxynucleotide triphosphate, dNTP, e.g. dATP, dCTP, dGTP, dTTP, dITP, dUTP, α-thio-dTNP, biotin-dUTP, fluorescein-dUTP, digoxigenin-dUTP.

Buffering agents, salt solutions and other additives of the present invention comprise those solutions useful in RT-PCR. Preferred buffering agents include e.g. TRIS, TRICINE, BIS-TRICINE, HEPES, MOPS, TES, TAPS, PIPES, CAPS. Preferred salt solutions include e.g. potassium chloride, potassium acetate, potassium sulphate, ammonium sulphate, ammonium chloride, ammonium acetate, magnesium chloride, magnesium acetate, magnesium sulphate, manganese chloride, manganese acetate, manganese sulphate, sodium chloride, sodium acetate, lithium chloride, and lithium acetate. Preferred additives include e.g. DMSO, glycerol, formamide, betain, tetramethylammonium chloride, PEG, Tween 20, NP 40, extoine, polyoles, $E.\ coli$ SSB protein, Phage T4 gene 32 protein, and BSA.

Additional compositional embodiments comprise other components that have been shown to reduce the inhibitory effect of reverse transcriptase on DNA polymerase, e.g. homopolymeric nucleic acids as described in EP 1050587 B1.

Further embodiments of this invention relate to methods for generating nucleic acids from an RNA template and further nucleic acid replication. The method comprises: a) adding an RNA template to a reaction mixture comprising at least one reverse transcriptase and/or mutants, variants and derivatives thereof and at least one nucleic acid polymerase, and/or mutants, variants and derivatives thereof, and an anionic polymer that is not a nucleic acid, and one or more oligonucleotide primers, and b) incubating the reaction mixture under conditions sufficient to allow polymerization of a nucleic acid molecule complementary to a portion of the RNA template. In a preferred embodiment the method includes replication of the DNA molecule complementary to at least a portion of the RNA template. More preferably the method of DNA replication is polymerase chain reaction (PCR). Most preferably the method comprises coupled reverse transcriptase-polymerase chain reaction (RT-PCR).

An anionic polymer according to the present invention is defined as any macromolecule that is not a nucleic acid and that comprises a net charge of at least −1 at the pH used in the enzymatic reactions according to the present invention and an equivalent amount of counter-cations. In one embodiment of the present invention, the net charge of the anionic polymers at the pH used in the enzymatic reaction is in the range from −1 to −10.000, preferable in the range of −5 to −5.000, more preferable in the range of −10 to −1.000 and most preferable in the range of −20 to −200. In all cases, an equivalent amount of counter-ions is present. In one embodiment of the present invention, the anionic polymer is a polysaccharide. In another embodiment of the present invention, the anionic polymer is a polypeptide. In yet another embodiment of the present invention, the anionic polymer is an acid or an anhydride. In a preferred embodiment, the anionic polymer is selected from the group consisting of dextran sulphate, sodium alginate, heparin, carrageen, sodium carboxymethylcellulose, polyphloretin phosphate, poly-L-glutamate, polyacrylic acid, poly(propylacrylic) acid, poly(methyl-vinyl-ether-maleic anhydride, or a mixture of two or more of these anionic polymers. The amount of anionic polymer used for RT-PCR may be greater than 1 pg/ml, preferably between 1 pg/ml to 1 mg/ml, more preferably between 10 pg/ml to 100 µg/ml, most preferably between 1 ng/m to 10 µg/ml.

Depending on the anionic polymer used, the concentration of the anionic polymer used for RT-PCR might vary.

In more specific embodiments, RT-PCR occurs between about 4° C. to about 100° C. Preferably, reverse transcription occurs between about 25° C. to about 75° C., followed by PCR occurring between about 40° C. to about 98° C. Under the most preferred conditions, reverse transcription occurs between about 37° C. to about 60° C., denaturation occurs at about 94° C., annealing occurs at about 60° C. and polymerization occurs at about 72° C.

DETAILED DESCRIPTION OF THE INVENTION

The present invention is directed to compositions and methods for use in the generation of nucleic acids from an RNA template, and particularly for reverse transcriptase-polymerase chain reaction (RT-PCR) production and analysis of nucleic acids. The invention provides compositions that include an anionic polymer that is not a nucleic acid in combination with one or more components useful in the generation of nucleic acids from an RNA template. Such components may include a reverse transcriptase, a DNA polymerase, one or more oligonucleotide primers, any one or more nucleotide bases, an appropriate buffering agent, a salt or other additives useful in RT or RT-PCR including nucleic acids such as homopolymeric nucleic acids as described in EP 1050587 B1.

Methods of the invention utilize anionic polymers in combination with other reagents to generate nucleic acid from an RNA template, and preferably also to replicate the newly synthesized nucleic acid. The compositions and methods of the present invention useful to generate, replicate, analyze, quantitate and otherwise manipulate nucleic acid molecules are most useful in coupled or uncoupled RT-PCR procedures.

RT-PCR is one molecular manipulation used to generate and replicate a nucleic acid derived from an RNA template. RT-PCR is described herein as an exemplary protocol capable of utilizing the compositions and methods of the present invention without limitation. It is understood by one of ordinary skill in the art that the present invention has utility in other processes which involve a combination of reverse transcriptase and DNA polymerase activity. RT-PCR involves two separate molecular syntheses: 1) the synthesis of cDNA from an RNA template; 2) the replication of the newly synthesized cDNA through PCR amplification.

Reverse Transcriptase Polymerase Chain Reaction (RT-PCR)

In RT-PCR, the reaction mixture is first incubated (in an appropriate buffering agent) at a temperature sufficient to allow synthesis of a DNA molecule complementary to at least a portion of an RNA template. Components of a reverse transcription reaction mixture typically include an RNA template, from which the complementary DNA (cDNA) is transcribed; a nucleic acid polymerase that exhibits reverse transcriptase activity; and the appropriate nucleotide building blocks needed for nucleic acid synthesis. For the purpose of this invention, cDNA is defined as any DNA molecule whose nucleic acid sequence is complementary to an RNA molecule. An RNA template is defined as any RNA molecule used to provide a nucleic acid sequence from which a cDNA molecule may be synthesized. The synthesis of cDNA from an RNA template is typically accomplished by utilizing a nucleic acid polymerase that exhibits reverse transcriptase activity. For the purpose of this invention, reverse transcriptase activity refers to the ability of an enzyme to polymerize a cDNA molecule from an RNA template, and reverse transcriptase broadly refers to any enzyme possessing reverse transcriptase activity. Reverse transcription typically occurs in a temperature range from about 20° C. to about 75° C., preferably from about 35° C. to about 70° C.

After reverse transcription of an RNA template to produce a cDNA molecule, the cDNA is incubated (in an appropriate buffering agent) under conditions sufficient for replication of the cDNA molecule. The reaction mixture may be the same as that of the previous reverse transcription reaction mixture, as employed in coupled (also called continuous, or one-step) RT-PCR, or the reaction mixture may comprise an aliquot of the previous reverse transcription reaction mixture and may be further modified for nucleic acid replication, as in uncoupled (or two-step) RT-PCR. Components of a replication reaction mixture typically include a nucleic acid template (in this instance the cDNA); a nucleic acid polymerase; and the appropriate nucleotide building blocks needed for nucleic acid synthesis. Nucleic acid replication refers to the polymerization of a nucleic acid whose sequence is determined by, and complementary to, another nucleic acid. DNA replication, as used herein, is synonymous with DNA amplification. Preferably, DNA amplification occurs repetitively, thus replicating both strands of the nucleic acid sequence, i.e., DNA complementary to the RNA template, and DNA whose nucleic acid sequence is substantially identical to the RNA template. Repetitive, or cyclic, DNA replication may be advantageously accomplished using a thermostable polymerase in a Polymerase Chain Reaction (PCR).

PCR is a technique well known in the art. PCR is used to amplify nucleic acids by subjecting a reaction mixture to cycles of: 1) nucleic acid denaturation, 2) oligonucleotide primer annealing, and 3) nucleic acid polymerization. Preferred reaction conditions for amplification comprise thermocycling, i.e., alternating the temperature of the reaction mixture to facilitate each of the steps of the PCR cycle. PCR is typically extended through multiple cycles of denaturation, annealing and replication, augmented (optionally and preferably) with an initial prolonged denaturation step and a final prolonged extension (polymerization) step. Thermocycling typically occurs within a temperature range of between about 23° C. to about 100° C., and preferably between about 37° C. to about 95° C. Nucleic acid denaturation typically occurs between about 90° C. to about 100° C., preferably about 94° C. Annealing typically occurs between about 37° C. to about 75° C., preferably about 55° C. Polymerization typically occurs between about 55° C. to about 80° C., preferably about 72° C. The number of thermocycles varies immensely, depending upon practitioner preference and the quantity of DNA product desired. Preferably, the number of PCR cycles ranges from about 5 to about 99, more preferably greater than about 20 cycles, most preferably about 40 cycles.

Template RNA

The template RNA can be any ribonucleic acid of interest, known or unknown to the practitioner. Template RNA can be artificially synthesized or isolated from natural sources. In some embodiments, the RNA template can be a ribonucleic acid such as RNA, mRNA, piRNA, tRNA, rRNA, ncRNA, shRNA, siRNA, snRNA, miRNA, snoRNA and viral RNA. Preferably, the RNA is mRNA. More preferably the RNA is biologically active or encodes a biologically active polypeptide.

Anionic Polymers

The present invention relates to the discovery that anionic polymers serve as an inhibition-relieving agent capable of suppressing, or otherwise reducing, the inhibition of nucleic acid replication by reverse transcriptase as observed in RT-PCR. An anionic polymer according to the present invention is defined as any macromolecule that is not a nucleic acid and that comprises a net charge of at least −1 at the pH used in the enzymatic reactions according to the present invention and an equivalent amount of counter-cations. In one embodiment of the present invention, the net charge of the anionic polymers at the pH used in the enzymatic reaction is in the range from −1 to −10.000, preferable in the range of −5 to −5.000, more preferable in the range of −10 to −1.000 and most preferable in the range of −20 to −200. In all cases, an equivalent amount of counter-ions is present. In one embodiment of the present invention, the anionic polymer is a polysaccharide. In another embodiment of the present invention, the anionic polymer is a polypeptide. In yet another embodiment of the present invention, the anionic polymer is an acid or an anhydride. In a preferred embodiment, the anionic polymer is selected from the group consisting of dextran sulphate, sodium alginate, heparin, carrageen, sodium carboxymethylcellulose, polyphloretin phosphate, poly-L-glutamate, polyacrylic acid, poly(propylacrylic) acid, poly(methyl-vinyl-ether-maleic anhydride, or a mixture of two or more of these anionic polymers. The amount of anionic polymer used for RT-PCR may be greater than 1 pg/ml, preferably between 1 pg/ml to 1 mg/ml, more preferably between 10 pg/ml to 100 μg/ml, most preferably between 1 ng/ml to 10 μg/ml. Depending on the anionic polymer used, the concentration of the anionic polymer used for RT-PCR might vary.

Reverse Transcriptases

Reverse transcriptases useful in the present invention may be any polymerase that exhibits reverse transcriptase activity. Several reverse transcriptases are known in the art and are commercially available. Preferred reverse transcriptases include: OmniScript (QIAGEN), Avian Myeloblastosis Virus reverse transcriptase (AMV-RT), Moloney Murine Leukemia Virus reverse transcriptase (MMLV-RT), Human Immunovirus reverse transcriptase (HIV-RT), EIAV-RT, RAV2-RT, *C. hydrogenoformans* DNA polymerase, Tth DNA polymerase, SuperScript I, SuperScript II, SuperScript III, and muntants, variants and derivatives thereof. It is to be understood that a variety of reverse transcriptases may be used in the present invention, including reverse transcriptases not specifically disclosed above, without departing from the scope or preferred embodiments thereof.

DNA Polymerases

DNA polymerases useful in the present invention may be any polymerase capable of replicating a DNA molecule. Preferred DNA polymerases are thermostable polymerases, which are especially useful in PCR. Thermostable polymerases are isolated from a wide variety of thermophilic bacteria, such as *Thermus aquaticus* (Taq), *Thermus brockianus* (Tbr), *Thermus flavus* (Tfl), *Thermus rubber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritime* (Tma), and other species of the *Thermotoga* genus, *Pyrococcus furiosus* (Pfu), *Pyrococcus woesei* (Pwo) and other species of the *Pyrococcus* genus, *Bacullus sterothermophilus* (Bst), *Sulfolobus acidocaldarius* (Sac), *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

Several DNA polymerases are known in the art and are commercially available. Preferably the thermostable DNA polymerase is selected from the group of Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT, DEEPVENT, and mutants, variants and derivatives thereof. It is to be understood that a variety of DNA polymerases may be used in the present invention, including DNA polymerases not specifically disclosed above, without departing from the scope or preferred embodiments thereof.

Oligonucleotide Primers

Oligonucleotide primers useful in the present invention may be any oligonucleotide of two or more nucleotides in length. Preferably, PCR primers are about 15 to about 30 bases in length, and are not palindromic (self-complementary) or complementary to other primers that may be used in the reaction mixture. Primers may be, but are not limited to, random primers, homopolymers, or primers specific to a target RNA template (e.g., a sequence specific primer). Oligonucleotide primers are oligonucleotides used to hybridize to a region of a target nucleic acid to facilitate the polymerization of a complementary nucleic acid. In preferred RT-PCR techniques, primers serve to facilitate reverse transcription of a first nucleic acid molecule complementary to a portion of an RNA template (e.g., a cDNA molecule), and also to facilitate replication of the nucleic acid (e.g., PCR amplification of DNA). Any primer may be synthesized by a practitioner of ordinary skill in the art or may be purchased from any of a number of commercial vendors. It is to be understood that a vast array of primers may be useful in the present invention, including those not specifically disclosed herein, without departing from the scope or preferred embodiments thereof.

Nucleotide Bases

Nucleotide bases useful in the present invention may be any nucleotide useful in the polymerization of a nucleic acid. Nucleotides may be naturally occurring, unusual, modified, derivative, or artificial. Nucleotides may be unlabeled, or detectably labeled by methods known in the art (e.g., using radioisotopes, vitamins, fluorescent or chemiluminescent moieties, digoxigenin). Preferably, the nucleotides are deoxynucleoside triphosphates, dNTPs (e.g., dATP, dCTP, dGTP, dTTP, dITP, dUTP, α-thio-dNTPs, biotin-dUTP, fluorescin-dUTP, digoxigenin-dUTP, 7deaza-dGTP). dNTPs are well known in the art and are commercially available.

Buffering Agents and Salt Solutions

Buffering agents and salts useful in the present invention provide appropriate stable pH and ionic conditions for nucleic acid synthesis, e.g., for reverse transcriptase and DNA polymerase activity. A wide variety of buffers and salt solutions and modified buffers are known in the art that may be useful in the present invention, including agents not specifically disclosed herein. Preferred buffering agents include, but are not limited to, TRIS, TRICINE, BIS-TRICINE, HEPES, MOPS, TES, TAPS, PIPES, CAPS. Preferred salt solutions include, but are not limited to solutions of potassium acetate, potassium sulphate, ammonium sulphate, ammonium chloride, ammonium acetate, magnesium chloride, magnesium acetate, magnesium sulphate, manganese chloride, manganese acetate, manganese sulphate, sodium chloride, sodium acetate, lithium chloride, and lithium acetate.

Other Additives Useful in RT-PCR

Other additives capable of facilitating reverse transcription, replication, and/or a combination of both reactions (e.g., agents for facilitating RT-PCR), other than those disclosed for the first time by this invention, are known in the art. In accordance with the compositions and methods of this invention, one or more of these additives may be incorporated in the present compositions to optimize the generation and replication of nucleic acids from an RNA template. Additives may be organic or inorganic compounds. Inhibition-reliving agents useful in the present invention include, but are not limited to polypeptides such as human serum albumin, bovine serum albumin (BSA), ovalbumin, albumax, casein, gelatine, collagen, globulin, lysozyme, transferrin, myoglobin, haemoglobin, α-lactalbumin, fumarase, glyceraldehyde-3-phosphate dehydrogenase (GAPDH), amyloglucosidase, carbonic anhydrase, β-lactoglobulin, aprotinin, soybean trypsin inhibitor, trypsinogen, phosphorylase b, myosin, actin, β-galactosidase, catalase, tryptic soy digestes, tryptose, lectins, *E. coli* single-stranded binding protein (SSB), phage T4 gene 32 protein, and the like, or fragments or derivatives thereof. Examples of non-polypeptide additives include, but are not limited to homopolymeric nucleic acids, tRNA, rRNA, sulphur-containing compounds, acetate-containing compounds, dimethylsulfoxide (DMSO), glycerol, formamide, betain, tetramethylammonium chloride (TMAC), polyethylene glycol (PEG), Tween 20, NP 40, ectoine, and polyoles. Preferred additives include homopolymeric nucleic acids, DMSO, glycerol, formamide, betain, TMAC, PEG, Tween 20, NP 40, extoine, polyoles, *E. coli* SSB protein, Phage T4 gene 32 protein, and BSA.

Reagent Kits for Coupled RT-PCR

A further aspect of the present invention is a reagent kit for coupled RT-PCR, comprising at least one reverse transcriptase, at least one DNA polymerase, and at least one anionic polymer that is not a nucleic acid. In such a reagent kit, said reverse transcriptase, DNA polymerase and anionic polymer may be combined in one container. Alternatively, said reverse transcriptase and DNA polymerase may be combined in one container and said anionic polymer may be in a second container. Alternatively, said reverse transcriptase and said anionic polymer may be combined in one container and said DNA polymerase may be in a second container. Alternatively, said DNA polymerase and said anionic polymer may be combined in one container and said reverse transcriptase may be in a second container. Alternatively, all three components may be in separate containers. Such a reagent kit may further comprise a mixture of two or more of dATP, dCTP, dGTP, and dTTP, and/or one or more additives useful in RT-PCR and/or a buffering agent. All components mentioned above may be in separate containers, or two or more of them may be combined in one container. Preferably, the two enzymes are combined in one container, either together with the anionic polymer or the anionic polymer being in a separate container, and a buffering agent, a dNTP mix, and one or more useful additives, if present, are provided in the kit in separate containers.

A further aspect of the present invention is the use of a composition or a reagent kit as above for coupled RT-PCR.

Particular embodiments of the present invention are as follows:

A composition suitable for the generation of nucleic acids from an RNA template, comprising an anionic polymer that is not a nucleic acid, one or more oligonucleotide primers, any one or more nucleotides or derivatives thereof, and two or more different polymerases, at least one of which has reverse transcriptase activity and at least one of which has nucleic acid polymerase activity.

The composition as above further comprising a buffering agent, a salt, and/or additives that are useful in RT-PCR.

The composition as above, wherein the anionic polymer is not a nucleic acids and comprises a net charge of at least −1 at the pH used in RT-PCR and comprises an equivalent amount of counter-ions.

The composition as above, wherein the net charge of the anionic polymer is in the range from −1 to −10.000, preferable in the range of −5 to −5.000, more preferable in the range of −10 to −1.000 and most preferable in the range of −20 to −200. In all cases, an equivalent amount of counter-ions is present.

The composition as above, wherein the anionic polymer is a polysaccharide, a polypeptide, an acid or an anhydride.

The composition as above, wherein the anionic polymer is selected from the group consisting of dextran sulphate, sodium alginate, heparin, carrageen, sodium carboxymethylcellulose, polyphloretin phosphate, poly-L-glutamate, polyacrylic acid, poly(propylacrylic) acid, poly(methyl-vinyl-ether-maleic anhydride, or a mixture of two or more of these anionic polymers.

The composition as above, wherein said polymerase exhibiting reverse transcriptase activity is selected from the group of OmniScript, AMV-RT, MMLV-RT, HIV-RT, EIAV-RT, RAV2-RT, *C. hydrogenoformans* DNA polymerase, SuperScript I, SuperScript II, SuperScript III, and/or mutants, variants and derivatives thereof.

The composition as above, wherein said polymerase exhibiting nucleic acid polymerase activity is selected from the group of Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT DNA polymerase, DEEPVENT DNA polymerase and/or mutants, variants and derivatives thereof.

A method for generating a nucleic acid from an RNA template comprising the steps:

a) adding said RNA template to a reaction mixture, said reaction mixture comprising at least one reverse transcriptase and/or mutants, variants and derivatives thereof and at least one nucleic acid polymerase, and/or mutants, variants and derivatives thereof, and an anionic polymer that is not a nucleic acid, and one or more oligonucleotide primers; and b) incubating said reaction mixture under conditions sufficient to allow polymerization of a nucleic acid molecule complementary to a portion of said RNA template.

The method as above, wherein the anionic polymer is not a nucleic acids and comprises a net charge of at least −1 at the pH used in RT-PCR and comprises an equivalent amount of counter-ions.

The method as above, wherein the net charge of the anionic polymer is in the range from −1 to −10.000, preferable in the range of −5 to −5.000, more preferable in the range of −10 to −1.000 and most preferable in the range of −20 to −200. In all cases, an equivalent amount of counter-ions is present.

The method as above, wherein the anionic polymer is a polysaccharide, a polypeptide, an acid or an anhydride.

The method as above, wherein the anionic polymer is selected from the group consisting of dextran sulphate, sodium alginate, heparin, carrageen, sodium carboxymethylcellulose, polyphloretin phosphate, poly-L-glutamate, polyacrylic acid, poly(propylacrylic) acid, poly(methyl-vinyl-ether-maleic anhydride, or a mixture of two or more of these anionic polymers.

The method as above, wherein said nucleic acid is DNA and said polymerase is DNA polymerase.

The method as above, wherein said DNA polymerase is selected from the group of Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT DNA polymerase, DEEPVENT DNA polymerase, and/or mutants, variants and derivatives thereof.

The method as above, wherein said reverse transcriptase is selected from the group of OmniScript, AMV-RT, M-MLV-RT, HIV-RT, EIAV-RT, RAV2-RT, *C. hydrogenoformans* DNA polymerase, SuperScript I, SuperScript II, SuperScript III, and/or mutants, variants and derivatives thereof.

A kit for performing coupled RT-PCR comprising at least one reverse transcriptase, at least one DNA polymerase, and at least one anionic polymer that is not a nucleic acid.

A kit for performing coupled RT-PCR, further comprising a mixture of two or more of dATP, dCTP, dGTP, and dTTP, and/or one or more additives useful in RT-PCR and/or a buffering agent.

EXAMPLES

Example 1

To demonstrate the specificity of RT-PCR is improved by the use of anionic polymers, increasing amounts of dextran sulphate 8000 (Sigma), were added to samples containing RNA from the influenza A virus. The matrix gene of the influenza A virus was selected as the RNA template for RT-PCR.

Viral RNA from the pandemic H1N1/09 virus, belonging to the group of influenza A viruses, was reacted in a final volume of 25 µl comprising 5 µl viral RNA eluate as template, reverse transcriptase (OmniScript, QIAGEN), 2.5 U of HotStar Fast Taq One-step RT-PCR buffer (QIAGEN) (1× final concentration) 0.4 mM each of dNTP mix, 0.6 µM each of forward (SEQ ID NO: 1) and reverse primer (SEQ ID NO: 2) for the matrix gene of influenza A virus and dextran sulphate at concentrations of 3.2 ng/ml to 640 ng/ml. The reverse transcription reaction mix was incubated at 50° C. for 30 minutes, followed by heating for 5 min at 95° C. After that, 45 cycles of 30 s at 94° C., 30 s at 50° C. and 1 min at 72° C. were run.

Figure 1:
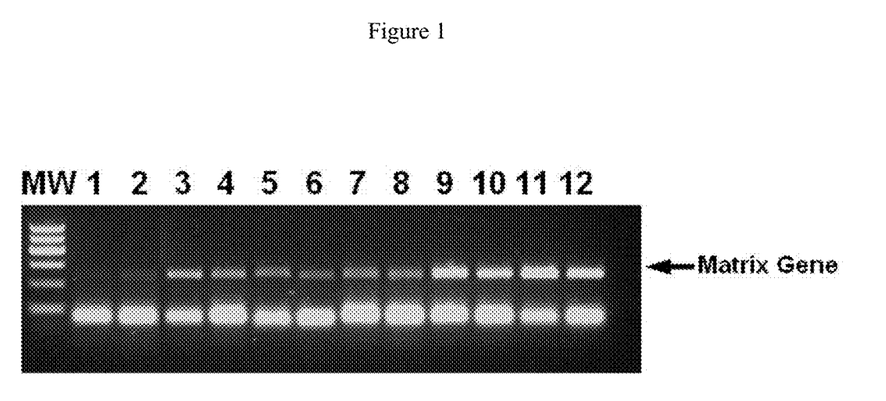
FIG. 1:
Viral RNA from the pandemic H1N1/09 virus was reverse transcribed and then PCR-amplified with gene specific primers for the Matrix gene of influenza Type A viruses. Dextran sulphate was either absent (lanes 1-2) or added to a final concentration of 3.2 ng/ml (lanes 3-4), 32 ng/ml (lanes 5-6), 160 ng/ml (lanes 7-8), 320 ng/ml (lanes 9-10) and 640 ng/ml (lanes 11-12).

The samples (in duplicate) were analyzed on an agarose gel (FIG. 1). A clear improvement in efficiency and specificity upon addition of dextran sulphate was observed. The yield of RT-PCR product significantly increased with increasing amounts of dextran sulphate. In this experiment, 320 and 640 ng/ml dextran sulphate showed the best results (lanes 9-12), but even very low concentrations of dextran sulphate (3.2 ng/ml, lanes 3-4) showed a clear positive effect compared to the control reaction (lanes 1-2), in which no dextran sulphate had been added to the RT-PCR.

Example 2

Figure 2:
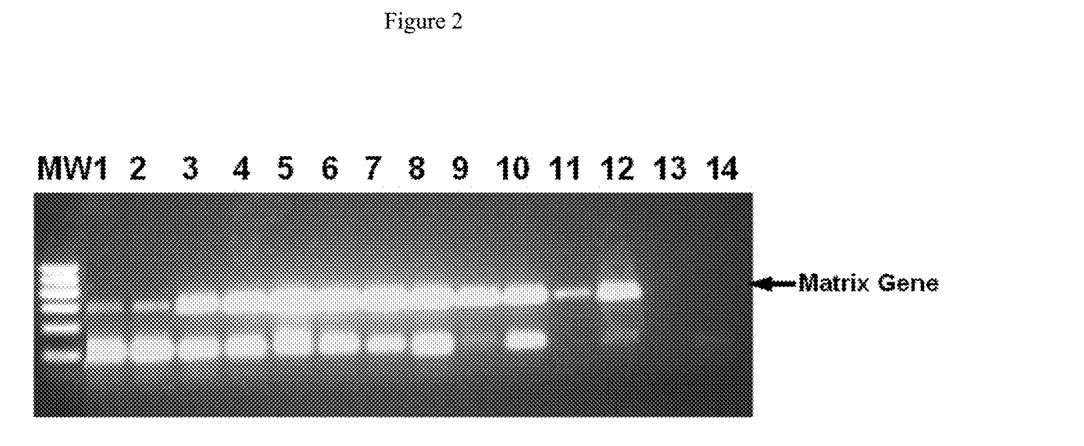
FIG. 2:
Viral RNA from the pandemic H1N1/09 virus was reverse transcribed and then PCR amplified with gene specific primers for the Matrix gene. Dextran sulphate was either absent (lanes 1-2) or added at a concentration of 320 ng/ml (lanes 3-4), 640 ng/ml (lanes 5-6), 1.6 µg/ml (lanes 7-8), 3.2 µg/ml (lanes 9-10), 6.4 µg/ml (lanes 11-12) and 16 µg/ml (lanes 13-14).

To determine whether dextran sulphate in higher concentrations could have a negative effect on the RT-PCR, higher concentrations of dextran sulphate were used. Reaction conditions were the same as described in Example 1, except for the concentration of dextran sulphate. The concentrations of dextran sulphate in this example were from 0.32 µg/ml to 16 µg/ml. The samples were again analyzed on an agarose gel (FIG. 2). Again, a clear improvement in efficiency and specificity upon addition of dextran sulphate was observed (lanes 3-12) compared to the control in which no dextran sulphate was added (lanes 1-2). Only at very high concentrations of dextran sulphate (16 µg/ml) (lanes 13-14) a negative effect on the RT-PCR could be detected as this concentration failed to yield any product in RT-PCR. However, the positive effect of dextran sulphate on efficiency and specificity could be detected over a wide range of concentrations (0.32 µg/ml-6.4 µg/ml) (lanes 3-12), demonstrating the robustness of the positive effect of anionic polymers on RT-PCR.

Example 3

To determine whether the positive effect of anionic polymers on RT-PCR were on the reverse transcription, on the replication of the cDNA or on both, a two-step RT-PCR was performed with adding the anionic polymers at the reverse transcription step, at the replication step or not at all.

Template RNA and all other reaction components were the same as in Example 1. The reverse transcription reaction was incubated for 30 min at 50° C. After that, the reverse transcription was stopped by cooling the reaction on ice. An aliquot of the reverse transcription (12.5 µl) was mixed with a 12.5 µl PCR master mix, including 2.5 U HotStar Taq Plus (QIAGEN), 0.6 µM of the primers (SEQ ID NO: 1 and 2), 0.4 mM dNTP mix and 1× One-Step RT-PCR buffer (QIAGEN). PCR was conducted with the cycling conditions as shown in Example 1. Dextran sulphate 8000 (Sigma) was added either to the reverse transcription reaction or to the PCR reaction to give a final concentration of 480 ng/ml. In a control reaction, no dextran sulphate was added.

Figure 3:
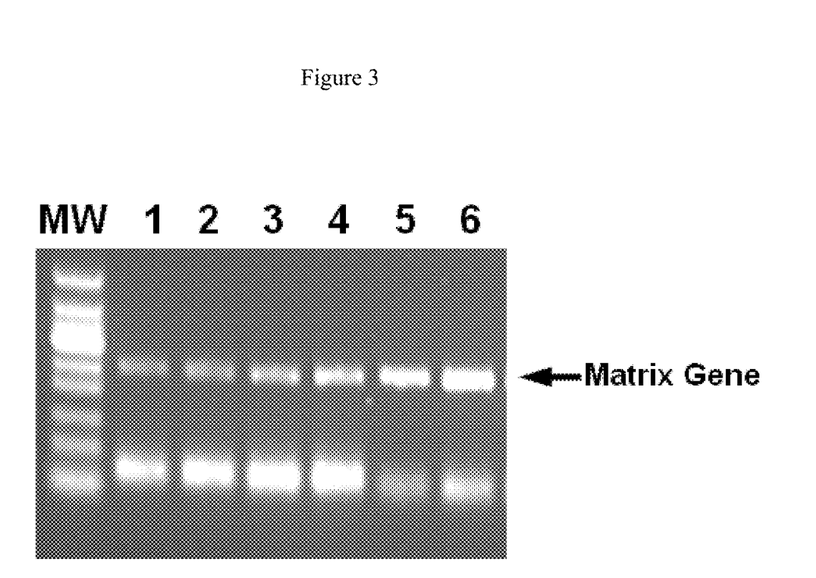
FIG. 3:
Viral RNA from the pandemic H1N1/09 virus was reverse transcribed with gene-specific primers for the Matrix gene. The RT mix was then mixed with PCR master mix to amplify the Matrix gene. The reaction was performed in duplicate either in the complete absence of dextran sulphate (lanes 1-2), with 480 ng/ml dextran sulphate only in the PCR (lanes 3-4) or with dextran sulphate in the reverse transcription (lanes 5-6).

The samples were analyzed in duplicate on an agarose gel (FIG. 3). In the reaction, in which no dextran sulphate was added, the yield of the matrix gene was very low and very high amounts of unspecific products were detectable (lanes 1-2). The addition of dextran sulphate to the PCR reaction slightly improved the yield of the matrix gene, but had little or no effect on the specificity. In contrast, addition of dextran sulphate to reverse transcription reaction gave significantly higher efficiency and specificity of the reaction. The positive effect of dextran sulphate is thus mainly due to its effect during the reverse transcription, although a slight positive effect could also be detected in the PCR.

Example 4

Figure 4:
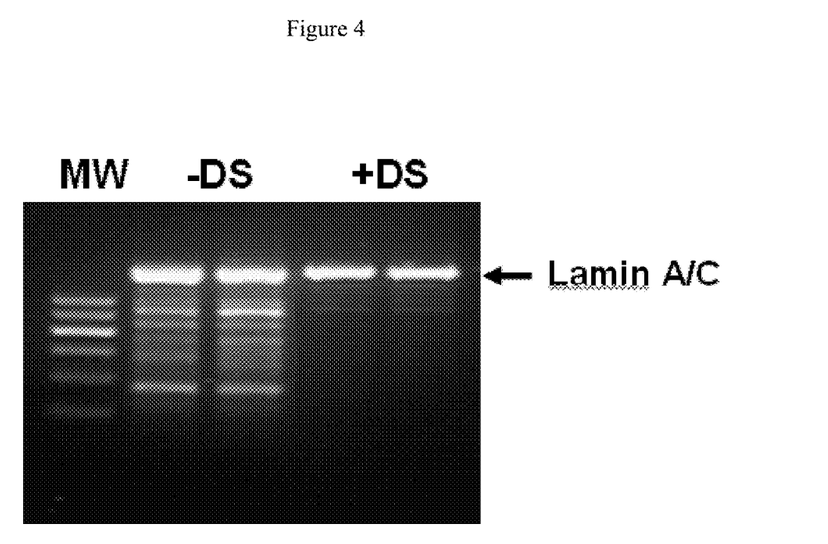
FIG. 4:
10 ng HeLa total RNA were reverse transcribed and then PCR amplified with gene-specific primers for Lamin A/C, either in the absence of dextran sulphate (lanes −DS) or with 640 ng/ml dextran sulphate (lanes+DS).
Figure 5:
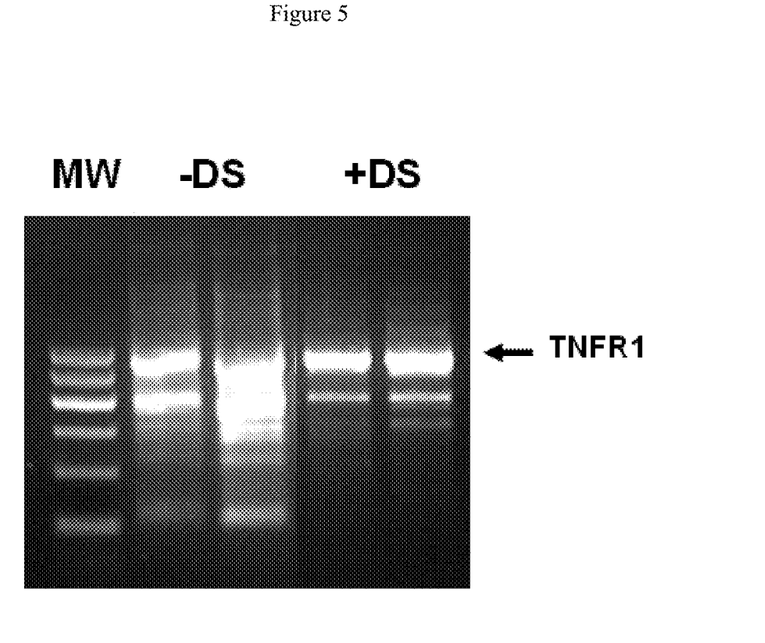
FIG. 5:
10 ng HeLa total RNA were reverse transcribed and then PCR amplified with gene-specific primers for TNFR1, either in the absence of dextran sulphate (lanes 1-2) or with 640 ng/ml dextran sulphate (lanes 3-4).

To demonstrate that not only viral RNA but also mRNA can serve as a template, 10 ng HeLa mRNA were used as a template for RT-PCR. Reaction conditions were the same as in Example 1, except that HeLa mRNA was used as template and primer pairs for the amplification of Lamin A/C (SEQ ID NOs: 3 and 4) and TNFR1 (SEQ ID NOs: 5 and 6), respectively, were used; and the annealing temperature in PCR was 55° C. instead of 50° C. As anionic polymer, 640 ng/ml dextran sulphate 8000 were used. Again, the samples were analyzed on an agarose gel in duplicate (FIG. 4 and FIG. 5). This example again proves the positive effect of anionic polymers on the efficiency and the specificity of the RT-PCR. While without the addition of dextran sulphate, in addition to the specific amplicon for Lamin A/C many unspecific amplicons could be detected (FIG. 4, lanes −DS), essentially only the specific amplicon for Lamin A/C could be detected when dextran sulphate was added to the RT-PCR (FIG. 4, lanes+DS). The situation is similar, when TNFR1 was amplified. Without the addition of dextran sulphate, in addition to the specific amplicon for TNFR1, many unspecific amplicons were detected (FIG. 5, lanes −DS), while a significant improvement on specificity and efficiency could be detected by the addition of dextran sulphate (FIG. 5, lanes+DS).

Example 5

Figure 6:
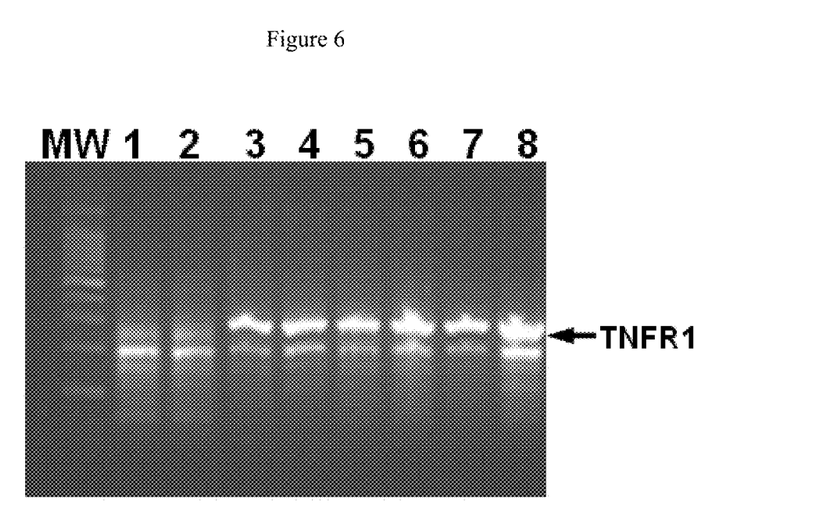
FIG. 6:
10 ng HeLa total RNA were reverse transcribed and then PCR amplified with gene-specific primers for TNFR1, either in the absence of sodium alginate (lanes 1-2) or with sodium alginate added to a final concentration of 40 ng/ml (lanes 3-4), 8 ng/ml (lanes 5-6) and 4 ng/ml (lanes 7-8).

To demonstrate that other anionic polymers in addition to dextran sulphate are suited for the improvement of specificity and efficiency, 1 ng, 200 pg and 100 pg, respectively, of sodium alginate were used as anionic polymer in the RT-PCR. Reaction conditions were the same as described in Example 4, except that sodium alginate was used as anionic polymer and that only the primer pairs for the amplification of TNFR1 (SEQ ID NOs: 5 and 6) were used. Again, the samples were analyzed in duplicate on an agarose gel (FIG. 6). The results clearly demonstrate that the addition of sodium alginate in various amounts also leads to an improvement of efficiency and specificity in RT-PCR. The results with sodium alginate as anionic polymer are similar to the results that were obtained with dextran sulphate as anionic polymer (FIG. 5).

Therefore, it could be shown that the improvement in efficiency and specificity of RT-PCR is a general feature of anionic polymers as two chemically distinct anionic polymers show a similar positive effect.

Sequences referred to in the examples:

SEQ ID NO: 1:
ATGAGYCTTYTAACCGAGGTCGAAACG

SEQ ID NO: 2:
TGGACAANCGTCTACGCTGCAG

SEQ ID NO: 3:
CATCCTCGCAAACCACCCACTCA

SEQ ID NO: 4:
CAGCGCCCACAAGCCACAGAG

SEQ ID NO: 5:
CAGCTCTCCGGCCTCCAGAAG

SEQ ID NO: 6:
TCCTCGGGTCCCCCTGTTGGT

---

The invention claimed is:

1. A method for the generation and amplification of nucleic acids by coupled reverse transcriptase-polymerase chain reaction, the method comprising steps of:

(a) incubating a reaction mixture comprising (i) a RNA template, (ii) at least one reverse transcriptase, (iii) at least one nucleic acid polymerase, (iv) an anionic polymer that is not a nucleic acid and is selected from the group consisting of sodium alginate, sodium carboxymethylcellulose, polyphloretin phosphate, poly-L-glutamate, polyacrylic acid, poly(propylacrylic acid), and poly(methyl-vinyl-ether-maelic anhydride), and (v) one or more oligonucleotide primers at a temperature sufficient to synthesize a DNA molecule that is complementary to at least a portion of the RNA template; and (b) thermocycling the reaction mixture from step (a) containing the DNA molecule to replicate the DNA molecule.

2. The method of claim 1, wherein the anionic polymer comprises an amount of counterions sufficient for the anionic polymer to maintain electric neutrality.

3. The method of claim 1, wherein said at least one nucleic acid polymerase is DNA polymerase.

4. The method of claim 3, wherein said DNA polymerase is selected from the group of Taq, Tbr, Tfl, Tru, Tth, Tli, Tac, Tne, Tma, Tih, Tfi, Pfu, Pwo, Kod, Bst, Sac, Sso, Poc, Pab, Mth, Pho, and ES4.

5. The method of claim 1, wherein said at least one reverse transcriptase is selected from the group consisting of, AMV-RT, M-MLV-RT, HIV-RT, EIAV-RT, RAV2-RT, and *C. hydrogenoformans* DNA polymerase.

* * * * *

SEQUENCE LISTING

```
<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1
atgagyctty taaccgaggt cgaaacg                                          27

<210> SEQ ID NO 2
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (8)..(8)
<223> OTHER INFORMATION: n is a, c, g, or t

<400> SEQUENCE: 2
tggacaancg tctacgctgc ag                                               22

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
catcctcgca aaccacccac tca                                              23

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
cagcgcccac aagccacaga g                                                21

<210> SEQ ID NO 5
<211> LENGTH: 21
<212> TYPE: DNA
<213> ORGANISM: Artificial Sequence
<220> FEATURE:
```

```
<223> OTHER INFORMATION: Primer

<400> SEQUENCE: 5
cagctctccg gcctccagaa g                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tcctcgggtc cccctgttgg t                                              21
```